United States Patent [19]

Drauz et al.

[11] Patent Number: 4,716,237
[45] Date of Patent: Dec. 29, 1987

[54] PROCESS FOR THE PRODUCTION OF 3-OXONITRILES

[75] Inventors: Karlheinz Drauz, Freigericht; Axel Kleemann, Hanau; Elisabeth Wolf-Heuss, Mosbach, all of Fed. Rep. of Germany

[73] Assignee: Degussa Aktiengesellschaft, Frankfurt, Fed. Rep. of Germany

[21] Appl. No.: 475,395

[22] Filed: Mar. 15, 1983

[30] Foreign Application Priority Data

Mar. 16, 1982 [DE] Fed. Rep. of Germany ....... 3209472

[51] Int. Cl.$^4$ .................. C07D 333/24; C07C 121/34; C07C 121/76
[52] U.S. Cl. ...................................... 549/72; 544/163; 546/168; 546/174; 546/245; 546/246; 546/328; 546/330; 548/180; 548/200; 548/204; 548/236; 548/503; 548/540; 548/561

[58] Field of Search ............... 260/465 R, 464, 465.1, 260/465 F, 465 G, 465.6, 465.7; 544/163; 546/168, 174, 245, 246, 328, 330; 548/180, 200, 204, 236, 503, 540, 561; 549/72, 76, 425, 426, 483, 496

[56] References Cited

FOREIGN PATENT DOCUMENTS 787858 12/1957 United Kingdom .

OTHER PUBLICATIONS

Kawase et al., Bulletin Chemical Society of Japan, vol. 35 (1962), pp. 1869–1871.
Levine et al., J. Amer. Soc., vol. 68 (1946), pp. 760–761.
Brown et al., Bull. Soc. Chem. France (1971) pp. 2195–2203.

Primary Examiner—Dolph H. Torrence
Attorney, Agent, or Firm—Cushman, Darby & Cushman

[57] ABSTRACT 3-oxonitriles are produced by reaction of carboxylic acid esters with carboxylic acid nitriles in the presence of 70 to 80% suspension of sodium hydride in white oil. The oxonitrile are intermediate products for the production of 3-oxocarboxylic acid amides or esters and pesticides.

17 Claims, No Drawings

PROCESS FOR THE PRODUCTION OF 3-OXONITRILES

BACKGROUND OF THE INVENTION

The invention is directed to a new process for the production of 3-oxonitriles by condensation of carboxylic acid esters with carboxylic acid nitriles as well as new 3-oxonitriles. It is known to produce 3-oxonitriles by dimerization of carboxylic acid nitriles in the presence of strong bases after saponification of the intermediately formed iminonitrile in yields of a maximum of 80% (Houben-Weyl, Vol. VII/2a, page 515). However, this process is only useful for the production of those compounds of general formula I below in which the group $R_1$ connected to the $$\overset{O}{\underset{}{\overset{\|}{C}}}$$

group and the —CH—$R_2$ group are the same. If different nitriles are employed there are obtained mixtures of products.

It is further known that the 3-oxonitriles can be obtained directly by condensation of carboxylic acid esters with carboxylic acid nitriles in the presence of strong bases. Strong CH-acid carboxylic acid nitriles, such as benzyl cyanide can be condensed with alcoholates. The yields are between 65 and 70%, based on the carboxylic acid ester employed.

The acylation of slightly acid aliphatic nitriles is accomplished only at elevated temperatures. Thus the yield deteriorates to 53% in the production of 2-benzoylpropionitrile because of undesired side reactions (Houben-Weyl VIII, page 573).

Furthermore, it is known that the condensation of aliphatic nitriles with carboxylic acid esters can only be carried out with finely divided sodium amide in liquid ammonia in preparative satisfactory yields (Houben-Weyl Vol. VIII, page 574, Levine J. Amer. Chem. Soc., Vol. 68, pages 760–761).

In agreement with this data the condensation of 2-methoxybenzoic acid methyl ester with acetonitrile using sodamide/liquid ammonia gives 2-methoxybenzoylacetonitrile in 84% yield, in contrast this same reaction using sodium hydride in benzene only leads to a 27.4% reaction yield. (Kawase, Bull, Chem. Soc. Japan, Vol. 35 (1962), pages 1869–1871.)

Furthermore, the reaction of ethyl propionate with acetonitrile using only 50 weight % sodium hydride is known. Thereby the sodium hydride in benzene at the boiling temperature is first treated with the acetonitrile and then the carboxylic acid ester dropped in. In this procedure there is the danger of self-condensation of the nitrile. Therefore the 3-oxonitrile is obtained in only 52% yield (Brown, Bull. Soc. Chem. France (1971), pages 2195–2203).

These yields are completely insufficient and permit no industrial scale synthesis of the 3-oxonitriles.

Further processes for the production of 3-oxonitriles are the reaction of chlorosulfonyl isocyanate with ketones and subsequent treatment of the N-chlorosulfonyl-3-oxoamide with dimethyl formamide with the setting free of the 3-oxonitrile (Synthesis) 1973, page 682), as well as the reaction of enamines with cyanogen chloride (Kuehne, J. Amer. Chem. Soc. Vol. 81 (1959), pages 5400–5404).

Both methods are very expensive preparatively and require considerable security precautions because of the dangerous nature of the materials employed. Besides the reaction yields at a maximum are 50%, so that there cannot be carried out on industrial syntheses.

There are also known special syntheses for individual 3-oxonitriles. Thus for example, pivaloylacetonitrile is obtained from pinacolone by chlorination and reaction of the monochloropinacolone with an alkali metal cyanide (German OS No. 2819264, the entire disclosure of which is hereby incorporated by reference including U.S. Pat. No. 4,062,861 mentioned therein).

This process is multistep and requires dealing with extremely toxic cyanides. Besides it is known that α-chloroketones, as represented by α-chloropinacolone are dangerous irritant materials.

SUMMARY OF THE INVENTION

It has now been found that there can be produced 3-oxonitriles of the general formula (I)

$$R_1-\overset{O}{\overset{\|}{C}}-\underset{R_2}{\overset{}{CH}}-CN \tag{I}$$

in which $R_1$ is a tertiary alkyl, cycloalkyl, aromatic or heteroaromatic group which in a given case can be substituted (e.g. the tertiary alkyl can have 4 to 7 or even up to 12 carbon atoms, the cycloalkyl can have 3 to 6 carbon atoms and can be substituted with one or more lower alkyl groups and/or one or more halogen atoms such as Cl, F, or Br, the aryl can be phenyl and can be substituted with at least one lower alkyl group and/or halogen atom, e.g. Cl, Br or F and/or lower alkoxy group and/or trihalomethyl and/or alkylmercapto group and the heteroaromatic group can be the furan group or the thienyl group and can be substituted with at least one lower alkyl group and/or halogen atom, e.g. Cl, Br, or F), and $R_2$ is a straight or branched alkyl group, an aryl group which in a given case can be substituted (e.g. the substituent can be e.g. where the halogen is Cl, Br, or F, or lower alkyl) furan, thienyl, or halogen substituted thienyl or furan, e.g. where the halogen is Cl, Br, or F or $R_2$ is hydrogen by reaction of a carboxylic acid of general formula (II)

$$R_1-COOR_3 \tag{II}$$

in which $R_3$ is a methyl or ethyl group with a carboxylic acid nitrile of the general formula (III)

$$R_2-CH_2-CN \tag{III}$$

where $R_1$ and $R_2$ are as defined above, in an inert solvent in the presence of sodium hydride if the sodium hydride is employed in the form of a 70–80% suspension in white oil, and this is present together with the ester of general formula (II).

The process of the invention can be carried out without the above-noted disadvantages and for the first time opens up a generally usable method for the production of 3-oxonitriles. It is one step, results in high yields and furnishes products of high purity.

The compounds of general formula I, a few of which are new are valuable intermediate products for the production of 3-ketocarboxylic acid-amides or -esters, heterocyclics and pesticides. An example is pivaloyl acetonitrile, an important intermediate product for an isoazole herbicide (German OS No. 2,436,179, German OS No. 2,819,264 and U.S. Pat. No. 4,062,861, the entire disclosure of these publications and patents are hereby incorporated by reference and relied upon). The new compounds can be used in the same manner as the compounds prepared in he two German OS and the United States patents and the same procedures can be used.

Under the carboxylic acid esters of general formula (II) those preferred are not enolizable. under the mentioned meanings for the symbol $R_1$ the term tert. alkyl groups stands for those groups in which the C-atom in the a-position contains no hydrogen atom. They can contain 4-12 carbon atoms, e.g. derived from the 2,2-dimethyl undecanoic acid and likewise the aromatic group can be substituted by groups which are inert to sodium hydride. There particularly belong thereto halogen atoms, alkoxy and alkylmercapto groups.

The cycloalkyl group can be substituted in the same manner and preferably has 3 to 6 members.

The heteroaromatic groups which can be present for $R_1$ and $R_2$ especially have 5 or 6 members and preferably have O-, S-, or N-atoms in the ring they can be anelated or condensed. Thus there can be present rings such as the pyridine ring, piperidine ring, thiazole ring, furan ring, thiophene ring, pyrane ring, morpholine ring, benzothiazole ring, pyrrole ring, benzopyrrole ring, quinoline ring, oxazole ring or the like.

Suitable carboxylic acid esters for example are the methyl or ethyl esters of pivalic acid, 2,2-dimethylbutyric acid, 2,2-dimethyl hexanoic acid, 2,2-dimethyl decanoic acid, 2,2-dimethyl undecanoic acid, 1-methylcyclopropanecarboxylic acid, 1-methylcyclobutanecarboxylic acid, 1-methylcyclopentanecarboxylic acid, 1-methylcyclohexanecarboxylic acid, cyclopropanecarboxylic acid, cyclohexanecarboxylic acid, 2,2-dichloro-1-methylcyclopropanecarboxylic acid, benzoic acid, 2-methylbenzoic acid, 3-methylbenzoic acid, 4-methylbenzoic acid, 2-ethylbenzoic acid, 4-butylbenzoic acid, 2,4-dimethylbenzoic acid, 2-fluorobenzoic acid, 3-fluorobenzoic acid, 4-fluorobenzoic acid, 2-chlorobenzoic acid, 3-chlorobenzoic acid, 4-chlorobenzoic acid, 2-bromobenzoic acid, 2,4-dichlorobenzoic acid, 3,4-dichlorobenzoic acid, 3,5-dichlorobenzoic acid, 2,4,6-trichlorobenzoic acid, 2-methyl-4-chlorobenzoic acid, 2-methoxybenzoic acid, 3-methoxybenzoic acid, 4-methoxybenzoic acid, 2-ethoxybenzoic acid, 3,4-dimethoxybenzoic acid, 3,4,5-trimethoxybenzoic acid, 2-trifluoromethylbenzoic acid, furan-2-carboxylic acid, furan-3-carboxylic acid, 5-bromo-2-methylfuran-3-carboxylic acid, thiophene-2-carboxylic acid, thiophene-3-carboxylic acid, 5-methylthiophene-2-carboxylic acid, 2-methylmercaptobenzoic acid, 2-pyridinecarboxylic acid, thiazole-4-carboxylic acid, oxazole-4-carboxylic acid, pyrrole-2-carboxylic acid.

Per mole of carboxylic acid ester employed advantageously there are used 1.5 to 2.1 moles, preferably 2 moles of the sodium hydride.

An inert solvent there are suitable used ethers, e.g. dioxane, dibutyl ether or aliphatic, cycloaliphatic or aromatic hydrocarbons such as hexane, decane, cyclohexane, benzene, toluene, or xylene.

The sodium hydride and the carboxylic acid ester are dissolved or suspended in the solvent and heated. Thereby it can be suitable to operate in an inert gas atmosphere, e.g. under nitrogen or argon. Then the carboxylic acid nitrile of general formula (II) is dropped into this heated, strongly stirred suspension.

In general formula (II) $R_2$ can have the above given meaning whereby in the case of the aromatic group, the heterocyclic group and the alkyl group there are possible the same substitutions as are given under $R_1$.

As carboxylic acid nitriles there can be used for example acetonitrile, propionitrile, butyronitrile, valeronitrile, benzyl cyanide, 2-chlorobenzyl cyanide, 4-chlorobenzyl cyanide, 4-fluorobenzyl cyanide, 2-bromobenzyl cyanide, 2-methylbenzyl cyanide, 4-methylbenzyl cyanide, thiophene-2-acetonitrile, thiophene-3-acetonitrile, furan-3-acetonitrile, 5-chlorothiophene-2-acetonitrile.

The amount of the carboxylic acid nitrile of general formula (III) employed in the reaction advantageously is between 1.0 and 2.1 moles per mole of carboxylic acid ester employed. Preferred is an amount between 1.5 and 2.0 moles of nitrile per mole of ester.

The reaction can be carried out in a temperature range between 50° and 110° C. Advantageously there is maintained a range between 60° and 100° C., preferably between 80° and 95° C. The initiation of the reaction can be made easier by the addition of a catalytic amount of an alcohol (methanol, ethanol, isopropanol, etc.). It is indicated by the escape of hydrogen. In the course of the reaction, the reaction speed (indicated through the amount of escaping $H_2$ per unit of time) can be controlled readily through the addition of nitrile.

The end of the reaction is indicated by the end of the development of hydrogen and through the complete reaction of the NaH in the reaction solution.

The working up is carried out in known manner for example, through stirring the reaction mixture (suspension) with a sufficiently large amount of water that the solids in the reaction mixture dissolve with the formation of two clear phases. The aqueous phase is separated off, the organic phase in a given case stirred with a further amount of water, the water phases combined, cooled and adjusted to a pH between 1 and 5 with aqueous mineral acid, e.g. hydrochloric acid or sulfuric acid, under cooling. Thereby the 3-oxonitrile separates out in solid form or as an oil.

The isolation of the product is carried out by filtering off the solids with suction or separating off the oil.

The product, in a given case, after a subsequent washing with water, is dried and, if necessary, further purified by recrystallization of fractionation.

If the precipitate only dissolved with difficulty in the reaction solution with the addition of water then it can be suitable to filter off this precipitate with suction, post wash with the solvent used, and introduce the product with very strong stirring into an aqueous mineral acid, e.g. hydrochloric acid, for neutralization. The amount of acid is suitably selected so that after complete reaction there is present a pH between 1 and 5 in the aqueous solution obtained. The preferred mineral acid is hydrochloric acid.

In a given case, it can be favorable in this procedure to even employ acetic acid or a mixture of acetic acid-mineral acid. There is then obtained the 3-oxonitrile in solid or liquid form, which, as described above, can be purified. Suitably in the working up the treatment with the acid should be carried out at a temperature which does not exceed 10° C., preferably 0° C.

The white oil used as suspension agent for the sodium hydride in the examples is the commercial product Shell Oudina 15 ® of the Shell Company. It consists of 65% paraffins and 35% naphthenes in a quality of DAB-8. It has a boiling point of 337° to 370° C./760 Torr.

Unless otherwise indicated all parts and percentages are by weight.

The process can comprise, consist essentially of, or consist of the stated steps with the materials recited.

The invention is explained further in the following examples.

DETAILED DESCRIPTION

Example 1

Pivaloylacetonitrile 55 grams of sodium hydride (as an 80 weight % suspension in white oil) were suspended in 500 ml of dry toluene, 106 grams (0.914 mole) of methyl pivalate added and the mixture heated to 85° C. Then under vigorous stirring there were dropped in 77 grams (1.87 moles) of acetonitrile within 4 hours. Stirring was continued subsequently at 85° C. until the end of the development of hydrogen. The thickly liquid reaction mass was cooled to room temperature, treated with 700 ml of water, stirred vigorously for 30 minutes and the two phases separated in a separatory funnel. The aqueous phase was acidified with 31 weight % of hydrochloric acid at a pH 1-2 and 0° C. The precipitated pivaloylacetonitrile was filtered off with suction, washed until neutral with ice water and dried to constant weight at 25 Torr and 40° C. There were obtained 106 grams (93% of theory) of analytically pure pivaloylacetonitrile having a melting point of 65°-68° C.

Analysis: $C_7H_{11}NO$ (125.0); Calculated: C 67.29, H 8.93, N 11.0; Found: C 67.17, H 8.86, N 11.9.

Example 2

Pivaloylacetonitrile

There were added in succession under a nitrogen atmosphere into 480 liters of toluene which had been dehydrated by azeotropic distillation 67.76 kg (584 moles) of methyl pivalate and 35 kg of an 80 weight % of sodium hydride in white oil. The suspension was heated to 85° C. and treated with 48.88 kg (1192 moles) of acetonitrile within 6 hours. The reaction mixture was stirred until the end of the development of hydrogen and stirred for a further 1.5 hours at 85° C., cooled to 25° C. and stirred with 500 ml of water. The aqueous phase was separated off, cooled to 0° C. and acidified to a pH 2 with 130 liters of concentrated hydrochloric acid under cooling and stirring. The precipitated produce was separated off, washed neutral with water and dried in a vacuum at 50 Torr and 40° C.

There were obtained 68.6 kg (94% of theory) of pivaloylacetonitrile having a melting point of 65°-68° C.

Example 3

1-Methylcyclopropanoylacetonitrile 128.2 grams (1 mole) of 1-methylcyclopropanecarboxylic acid methyl ester and 60 grams (1 mole) of sodium hydride, 80 weight % in white oil were heated in 750 ml of dry toluene to 80° C. and 82.1 grams (2 moles) of acetonitrile dropped in with vigorous stirring within 1 hour. Stirring was continued at this temperature until the end of the develoment of hydrogen. After cooling to room temperature the reaction was treated with, in all, 1 liter of water, stirred and after phase separation the aqueous phase adjusted to pH 1.5 with hydrochloric acid. Thereby the temperature was held in a range between 0° and +5° C.

The oil which deposited was separated off, the water phase extracted with 500 ml of methylene chloride, the organic phases combined, dried over sodium sulfate and the solvent distilled off.

The oily residue was fractionated in a vacuum. 104.9 grams (85% of theory) of 1-methylcyclopropanoylacetonitrile came over at 130°-132° C./20 mm.

Analysis: $C_7H_9NO$ (123.16); Calculated: C 68.30, H 7.40, N 11.40; Found: C 68.31, H 7.44, N 11.52.

$^1$H-NMR (CDCl$_3$): δ=3.70 (s, 2H) $\underline{CH_2}$—CH; 1.45 (S, 3H) $\underline{CH_3}$; 1.4–0.65 ppm (m, 5H); Cyclopropyl.

Example 4

(2',2'-Dichloro-1'-methyl)cyclopropanoylacetonitrile 183 grams (1 mole) of 2,2-dichloro-1-methylcyclopropanecarboxylic acid methyl ester and 60 grams (2 moles) of 80 weight % sodium hydride were reacted with 82.1 grams (2 moles) of acetonitrile in 750 ml of dry toluene as described in Example 3.

After the distillation there were obtained 117.6 grams (61.2% of theory) of (2,2-dichloro-1-methyl)cyclopropanoylacetonitrile having a boiling point of 102°-103° C. at 0.5 Torr.

Analysis: $C_7H_7Cl_2NO$ (192.05); Calculated: C 43.77, H 3.67, N 7.29, Cl 36.92; Found: C 44.18, H 4.21, N 7.63, Cl 36.91.

$^1$H-NMR (CDCl$_3$) δw=4.95, 4.90 (S, 2H) $\underline{CH_2}$—CH; 1.95 (AB,2H) C (Cl$_2$)—$\underline{CH_2}$; 1.70 ppm (S,3H) C—$\underline{CH_3}$.

Example 5

2-Thiophenoylacetonitrile 78.1 grams (0.5 mole) of thiophene-2-carboxylic acid ethyl ester and 30 grams (1 mole) of sodium hydride (80% in suspension in white oil) were reacted with 41.5 grams (1 mole) of acetonitrile in 500 ml of dry toluene. There were obtained 70.0 grams (92.6% of theory) of 2-thiophenoylacetonitrile having a melting point of 110° C.

Analysis: $C_7H_5NOS$ (151.18); Calculated: C 55.61, H 3.33, N 9.27, S 21.21; Found: C 55.49, H 3.46, N 9.11, S 21.05.

$^1$H-NMR (DMSO/$d_6$): δ=8.1–7.0 (m, 3H) H Thiophene, 4.33 ppm (S, 2H) CH$_2$CN.

Example 6

2-Furanoylacetonitrile 63.05 grams (0.5 mole) of furan-2-carboxylic acid ethyl ester and 30.0 grams (1 mole) of sodium hydride (80 weight % suspension in white oil) were reacted with 41 grams (1 mole) of acetonitrile in 500 ml of toluene with the addition of 1 ml of methanol at 90° C. After 3 hours reaction time the toluene was distilled off, the residue stirred with 500 ml of water, acidified with hydrochloric acid to pH 1.5 and the precipitated product filtered off with suction and recrystallized from methanol. There were obtained 51.3 grams (76% of theory) of 2-furanoylacetonitrile having a melting point of 74°-75° C.

Analysis: $C_7H_5NO_2$ (135.12); Calculated: C 62.33, H 3.73, N 10.36; Found: C 61.86, H 3.48, N 10.11.

$^1$H-NMR (CDCl$_3$): δ=7.69 (S, 1H), 7.38 (d, 1H); 6.63 (m, 1H) H$_{Furan}$; 4.0 ppm (S, 2H) $\underline{CH_2}$—CN.

Example 7

Benzoylacetonitrile 70 grams (0.5 mole) of ethyl benzoate were heated with 30 grams (1 mole) of sodium hydride (80 weight % suspension in white oil) in 500 ml of dry toluene to 75°–80° C. Within 2 hours there were dropped in 41 grams (1 mole) of acetonitrile and the mixture stirred at 85° C. until the end of the development of hydrogen. The reaction mixture was cooled to room temperature, filtered with suction and the solid material stirred in a mixture of 9 parts of glacial acetic acid and 1 part of 31 weight % hydrochloric acid at 0° C. and this reaction mixture subsequently poured on 700 ml of ice.

The precipitated solids were filtered off with suction, washed neutral with water and dried at 50 Torr 65° C. until constant weight.

There were obtained 64.5 grams (89% of theory) of benzoylacetonitrile having a melting point of 80°–82° C.

Example 8

4'-Methoxybenzoylacetonitrile 166.2 grams (1 mole) of 4-methoxybenzoic acid methyl ester and 60 grams (2 moles) of sodium hydride (80 weight % suspension in white oil) were heated to 65° C. in 750 ml of dry toluene. Within 2 hours there were dropped in 82.1 grams (2 moles) of acetonitrile at 85° C. and then stirring was continued for a further 20 hours at 90° C. The precipitate was filtered off with suction, 200 ml of glacial acetic acid slowly stirred in with cooling and subsequently the mixture was added to 1 liter of ice water. The precipitated crystal mass was filtered off with suction, post washed with water and recrystallized from acetone. There were thus obtained 149 grams (85% of theory) of 4-methoxybenzoylacetonitrile having a melting point of 127°–129° C.

Example 9

2,4,4-Trimethyl-3-oxopentanenitrile 234.6 grams (2 moles) of methyl pivalate and 120 grams (2 moles) of sodium hydride (80 weight % suspension in white oil) were heated to 90° C. in 1500 ml of dry toluene. There were dropped in at this temperature after addition of 1 ml of methanol 233.3 grams (2 moles) of propionitrile within 2.5 hours. After the end of the development of hydrogen the suspension was extracted with a total of 1200 ml of water and after phase separation the aqueous phase was acidified with concentrated HCl to a pH of 2. The deposited oil was separated off, the water phase extracted with chloroform, the organic extracts combined, dried and concentrated. The residue was fractionated in a water jet vacuum. 2,4,4-trimethyl-3-oxopentanenitrile came over at 87° C./11 Torr in an amount of 226.1 grams (81.2% of theory).

Example 10

4,4-Dimethyl-2-ethyl-3-oxopentanenitrile 58 grams (0.5 mole) of methyl pivalate, 30 grams (1 mole) of 80 weight % NaH in white oil, and 69 grams (1 mole) of n-butyronitrile in toluene were reacted in the manner described in Example 9. After working up the crude product obtained was fractionated in the water jet vacuum. 50 grams (65% of theory) of 4,4-dimethyl-2-ethyl-3-oxopentanenitrile came over at a boiling point of 98°–99° C./15 Torr.

Analysis: $C_9H_{15}NO$ (153.2); Calculated: C 70.5, H 9.9, N 9.14; Found: C 70.48, H 10.12, N 9.18.

$^1$H-NMR (CDCl$_3$): δ=3.83 (t, 1H) CO—CH; 1.91 (q, 2H) CH$_2$—CH$_3$; 1.23 (S, 9H) C (CH$_3$)$_3$; 1.06 ppm (t, 3H) CH$_2$—CH$_3$

Example 11

4,4-Dimethyl-2-phenyl-3-oxopentanenitrile 116 grams (1 mole) of methyl pivalate, 60 grams (2 moles) of sodium hydride (80 weight % suspension in white oil) and 234.3 grams (2 moles) of benzyl cyanide were reacted in 750 ml of dry toluene at 60° C. until the end of the evolution of hydrogen. There were added 500 ml of water to the cooled reaction solution, the mixture stirred and the aqueous phase acidified with HCl to pH 3 after the separation and then extracted with chloroform. After concentrating the chloroform the oil residue was fractionated at 0.6 Torr. 110.6 grams (55% of theory) of 4,4-dimethyl-2-phenyl-3-oxopentanenitrile came over at 111° C.

The spectroscopic and analytical data agreed with those of theory.

Example 12

4,4-Dimethyl-2-(3'-thienyl)-3-oxopentanenitrile 116 grams (1 mole) of methyl pivalate, 60 grams (2 moles) of sodium hydride (80 weight % in white oil) and 184.7 grams (1.5 moles) of thiophene-3-acetonitrile were reacted as described in Examples 8 in 750 ml of dry toluene. The reaction time was 24 hours. The crystalline crude proudct was distilled for purification.

There were obtained 109 grams (53% of theory) of 4,4-dimethyl-2-(3'-thienyl)-3-oxopentanenitrile at a boiling point of 112° C./0.4 Torr and the product had a melting point of 45°–47° C.

Analysis: $C_{11}H_{13}NOS$ (207.3); Calculated: 63.73, H 6.32, N 6.76, S 15.47; Found: 63.60, H 6.34, N 6.64, S 14.90.

$^1$H-NMR (CDCl$_3$): δ=7.4–7.0 (m, 3H) H$_{Thiophene}$; 5.33 (S, 1H) CH—CN; 1.22 ppm (S, 9H) C (CH$_3$)$_3$.

Example 13

2-Benzoylpropionitrile 137 grams (1 mole) of methyl benzoate and 60 grams (2 moles) of 80 weight % sodium hydride in white oil were heated to 75° C. in 750 ml of toluene and treated at this temperature within 1.5 hours with 110.2 grams (2 moles) of propionitrile. The mixture was stirred at 85°–90° C. until the end of the development of hydrogen. The reaction mixture was filtered off with suction and the precipitate suspended in 1000 ml of water and acidified with hydrochloric acid to pH 2 with vigorous stirring. The precipitated oil was separated off, the aqueous phase extracted with a total of 300 ml of toluene. The combined organic phases were dried over sodium sulfate, concentrated and the oil fractionated in a vacuum.

There were obtained 97 grams (61% of theory) of 2-benzoylpropionitrile of boiling point 110° C./0.6 Torr in the distillation Analysis: $C_{10}H_9NO$ (159.1); Calculated: C 75.45, H 5.70, N 8.80; Found: C 75.41, H 5.89, N 8.91.

Example 14

4,4-Dimethyl-2-(4'-chlorophenyl)-3-oxopentanenitrile 116 grams (1 mole) of methyl pivalate, 60 grams (2 moles) of 80 weight % sodium hydride in white oil and 151.5 grams (1.5 moles) of 4-chlorobenzyl cyanide were reacted as described in Example 8.

After working up there were obtained 147.4 grams (62.2% of theory) of 4,4-dimethyl-2-(4'-chlorophenyl)-3-oxopentanenitrile as a viscous oil.

Analysis: $C_{13}H_{14}ClNO$ (235.45); Calculated: C 66.24, H 5.97, N 5.94, Cl 15.05; Found: C 66.44, H 6.06, N 6.26, Cl 15.74.

$^1$H-NMR (CDCl$_3$): $\delta = 7.37$ (S, 4H) H$_{Ar}$; 5.20 (S, 1H) CH—CN; 1.20$_{ppm}$ (S, 9H) C (CH$_3$)$_3$.

the entire disclosure of German priority application No. P3209472.8 is hereby incorporated by reference.

What is claimed is:

1. A process for the production of a 3-oxonitrile of the formula

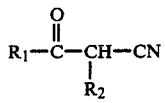

in which R$_1$ is a tertiary alkyl group, cycloalkyl group, aromatic hydrocarbon group or heteroaromatic group which is a pyridine group, piperidine group, thiazole group, furan group, thiophene group, pyrane group, morpholine group, benzothiazole group, pyrrole group, benzopyrrole group, quinoline group or oxazole group, or such a group containing a substituent non-reactive with sodium hydride and R$_2$ is hydrogen, an alkyl group having 1 to 4 carbon atoms or such an alkyl group substituted by an aryl group, an aryl group containing a substituent non-reactive with sodium hydride, a heteroaromatic group, which is a pyridine group, piperidine group, thiazole group, furan group, thiophene group, pyrane group, morpholine group, benzothiazole group, pyrrole group, benzopyrrole group, quinoline group or oxazole group or a heteroaromatic group containing a substituent non-reactive with sodium hydride, comprising reacting a carboxylic acid ester of the formula

in which R$_3$ is methyl or ethyl, with a carboxylic acid nitrile of the formula

in an inert solvent with sodium hydride, the sodium hydride being added as a 70–80% suspension in white oil.

2. A process according to claim 1 where R$_1$ is tertiary alkyl of 4 to 12 carbon atoms, cycloalkyl of 3 to 6 carbon atoms, cycloalkyl of 3 to 6 carbon atoms substituted with at least one member of the group consisting of lower alkyl and halogen, phenyl, phenyl substituted with at least one member of the group consisting of lower alkyl, halogen, lower alkoxy and trihalomethyl, heteroaromatic having 5 to 6 atoms in the ring and wherein the hetero atom or atoms are selected from the group consisting of oxygen, sulfur and nitrogen or such a heteroaromatic group having at least one substituent selected from the group consisting of lower alkyl and halogen and R$_2$ is hydrogen, alkyl having 1 to 4 carbon atoms, phenyl substituted with at least one member of the group consisting of lower alkyl and halogen, heteroaromatic having 5 to 6 atoms in the ring and where the hetero atom or atoms are selected from the group consisting of oxygen, sulfur and nitrogen or such a heteroaromatic group having at least one substituent selected from the group consisting of lower alkyl and halogen.

3. A process according to claim 2 wherein the tertiary alkyl has 4 to 7 carbon atoms and any heteroaromatic group present is a furan group, a thiophene group or a furan or thiophene group substituted by at least one member of the group consisting of lower alkyl and halogen.

4. A process according to claim 1 wherein the compound of formula (I) is pivaloylacetonitrile, 1'-methylcyclopropanoylacetonitrile, (2',2'-dichloro-1'-methyl)-cyclopropanoylacetonitrile, 2-thiophenoylacetonitrile, 2-furanoylacetonitrile, benzoylacetonitrile, 4-methoxybenzoylacetonitrile, 2,4,4-trimethyl-3-oxopentanenitrile, 4,4-dimethyl-2-ethyl-3-oxopentanenitrile, 4,4-dimethyl-2-phenyl-3-oxopentanenitrile, 4,4-dimethyl-2-(3'-thienyl)-3-oxopentanenitrile, 2-benzoylpropionitrile or 4,4-dimethyl-2-(4'-chlorophenyl)-3-oxo-pentanenitrile.

5. A process according to claim 1 wherein the inert solvent is toluene.

6. A process according to claim 5 wherein the sodium hydride and the ester of formula (II) are used in a molar ratio of 1.5 to 2.1:1.

7. A process according to claim 1 wherein the sodium hydride and the ester of formula (II) are used in a molar ratio of 1.5 to 2.1:1.

8. A process according to claim 7 wherein the ratio is 2:1.

9. A process according to claim 1 wherein the nitrile of formula (III) and the ester of formula (II) are employed in a molar ratio of 1.0 to 2.1:1.

10. A process according to claim 5 wherein the nitrile of formula (III) and the ester of formula (II) are employed in a molar ratio of 10 to 2.1:1.

11. A process according to claim 6 wherein the nitrile of formula (III) and the ester of formula (II) are employed in a molar ratio of 1.0 to 2.1:1.

12. A process according to claim 1 wherein the nitrile of formula (III) and the ester of formula (II) are employed in a molar ratio 1.5 to 2.0:1.

13. A process according to claim 12 wherein the sodium hydride and the ester of formula (II) are used in a molar ratio of 2:1.

14. A process according to claim 1 wherein the temperature is between 50° and 110° C.

15. A process according to claim 14 wherein the temperature is 60° to 100° C.

16. A process according to claim 14 wherein the temperature is between 80° and 95° C.

17. A process according to claim 1 wherein the reaction is carried out in the presence of a catalytic amount of an alcohol.

* * * * *